(12) United States Patent
Howell et al.

(10) Patent No.: US 11,520,320 B2
(45) Date of Patent: Dec. 6, 2022

(54) SYSTEM FOR OPTIMIZING THE ORGANIZATION OF COMPONENTS FOR THE MANUFACTURE OF WOOD PRODUCTS

(71) Applicant: Michael Weinig, Inc., Mooresville, NC (US)

(72) Inventors: Jason F. Howell, Mooresville, NC (US); Daniel Dew, Mooresville, NC (US)

(73) Assignee: MICHAEL WEINIG, INC, Mooresville, NC (US)

( * ) Notice: Subject to any disclaimer, the term of this patent is extended or adjusted under 35 U.S.C. 154(b) by 328 days.

(21) Appl. No.: 16/650,731

(22) PCT Filed: Mar. 20, 2020

(86) PCT No.: PCT/US2020/023905
§ 371 (c)(1),
(2) Date: Mar. 25, 2020

(87) PCT Pub. No.: WO2020/191311
PCT Pub. Date: Sep. 24, 2020

(65) Prior Publication Data
US 2021/0365014 A1 Nov. 25, 2021

Related U.S. Application Data

(60) Provisional application No. 62/821,387, filed on Mar. 20, 2019.

(51) Int. Cl.
*G06F 17/00* (2019.01)
*G05B 19/418* (2006.01)
(Continued)

(52) U.S. Cl.
CPC ... *G05B 19/41865* (2013.01); *G06K 7/10297* (2013.01); *G06K 7/10366* (2013.01);
(Continued)

(58) Field of Classification Search
CPC ......... G05B 19/41865; G06K 7/10297; G06K 7/10366; G06K 7/1413
(Continued)

(56) References Cited

U.S. PATENT DOCUMENTS

| 6,120,628 A * | 9/2000 | Pritelli ...................... B27B 1/00 |
| | | 156/266 |
| 7,966,714 B2 * | 6/2011 | Dick ........................ B27M 1/08 |
| | | 29/897 |

(Continued)

OTHER PUBLICATIONS

Patent Cooperation Treaty; International Search Report and Written Opinion cited in PCT/US20/23905 dated Jun. 15, 2020, 13 pages.

*Primary Examiner* — Ahshik Kim
(74) *Attorney, Agent, or Firm* — Shumaker, Loop & Kendrick, LLP; Patrick B. Horne

(57) ABSTRACT

A system optimizes the organization of components for the manufacture of wood products. The system includes memory devices and processing devices operatively coupled to the memory device, wherein the one or more processing devices are configured to execute computer-readable computer program code to receive a plurality of job orders for distinct wood products having varying components; optimize cutting of all components for the plurality of job orders to minimize waste of source materials, thereby resulting in a plurality of components for the plurality of job orders; track each component electronically in order to identify each component at a final cutting machine location; and affix a unique indicator on each component indicating both a receptacle and a receptacle portion corresponding to each component, thereby optimizing organization of all the compo- (Continued)

nents by at least one of job, distance from machine to receptacle, and distance from receptacle to assembly location.

20 Claims, 3 Drawing Sheets

(51) Int. Cl.
   *G06K 7/10* (2006.01)
   *G06K 7/14* (2006.01)
   *G06Q 10/00* (2012.01)

(52) U.S. Cl.
   CPC ......... *G06K 7/1413* (2013.01); *G06K 7/1417* (2013.01); *G06Q 10/30* (2013.01); *G05B 2219/45229* (2013.01)

(58) Field of Classification Search
   USPC ....................................................... 700/107
   See application file for complete search history.

(56) References Cited

U.S. PATENT DOCUMENTS

| | | | |
|---|---|---|---|
| 8,783,140 B2* | 7/2014 | Dick | B27B 31/06 83/13 |
| 10,453,153 B2* | 10/2019 | Heape | G06Q 50/04 |
| 2005/0115375 A1 | 6/2005 | Dick et al. | |
| 2007/0270996 A1* | 11/2007 | Roise | G06Q 10/06 700/171 |
| 2015/0217475 A1 | 8/2015 | Hass et al. | |
| 2017/0031350 A1 | 2/2017 | Dew et al. | |
| 2020/0342585 A1* | 10/2020 | Voyer | H04N 5/2354 |

\* cited by examiner

SYSTEM FOR OPTIMIZING THE ORGANIZATION OF COMPONENTS FOR THE MANUFACTURE OF WOOD PRODUCTS

CROSS-REFERENCE TO RELATED APPLICATIONS

This application is a non-provisional application claiming priority to and the benefit of U.S. Provisional Application No. 62/821,387, filed Mar. 20, 2019, entitled "SYSTEM FOR OPTIMIZING THE ORGANIZATION OF COMPONENTS FOR THE MANUFACTURE OF WOOD PRODUCTS", and also claiming priority to PCT/US2020/023905, filed Mar. 20, 2020, entitled "SYSTEM FOR OPTIMIZING THE ORGANIZATION OF COMPONENTS FOR THE MANUFACTURE OF WOOD PRODUCTS, the entirety of each are expressly incorporated by reference herein.

TECHNICAL FIELD AND BACKGROUND OF THE INVENTION

This application relates to the manufacture of wood products, such as solid wood products. More specifically, the application relates to the use of computer-machine networked systems that are used to optimize organization of components for the manufacture of wood products.

BRIEF SUMMARY

According to embodiments of the invention, systems, methods and computer program products are provided for optimizing the organization of components for the manufacture of wood products. For example, a system is provided that includes (a) one or more memory devices; and (b) one or more processing devices operatively coupled to the memory device, wherein the one or more processing devices are configured to execute computer-readable computer program code to: (i) receive a plurality of job orders for distinct wood products having varying components; (ii) optimize cutting of all components for the plurality of job orders to minimize waste of source materials, thereby resulting in a plurality of components for the plurality of job orders; (iii) track each component electronically in order to identify each component at a final cutting machine location; and (iv) affix a unique indicator on each component indicating both a (i) receptacle and a (ii) receptacle portion corresponding to each component, thereby optimizing organization of all the components by at least one of job, distance from machine to receptacle, and distance from receptacle to assembly location.

In some embodiments, the system includes one or more production devices operatively coupled with the one or more processing devices. In some such embodiments, the one or more processing devices are configured to execute computer-readable computer program code to control one or more actions of the one or more production devices.

In some embodiments, the one or more processing devices are configured to execute computer-readable computer program code to create a plurality of unique indicators for affixation on each component.

In some embodiments, the one or more processing devices are configured to execute computer-readable computer program code to track each component electronically by scanning each component to identify each component by visible characteristics or collocated identifier.

In some embodiments, the one or more processing devices are configured to execute computer-readable computer program code to track each component electronically by scanning a collocated identifier comprising an RFID or Nearfield communication device.

In some embodiments, the one or more processing devices are configured to execute computer-readable computer program code to track each component electronically by scanning a readable indicia comprising a barcode or Quick Response (QR) code.

The features, functions, and advantages that have been discussed may be achieved independently in various embodiments of the present invention or may be combined with yet other embodiments, further details of which can be seen with reference to the following description and drawings.

BRIEF DESCRIPTION OF THE DRAWINGS

Figure 1:
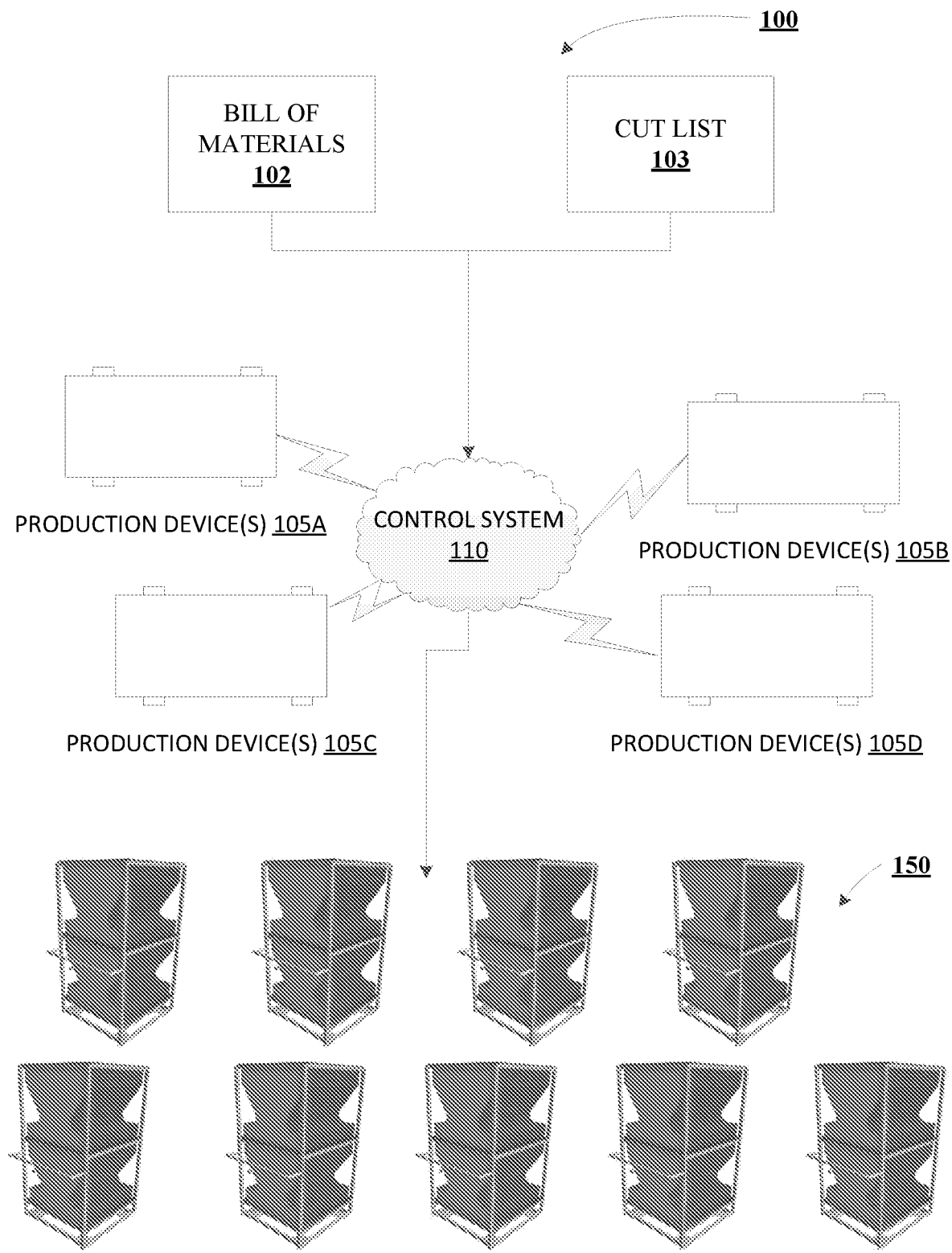
Figure 2:
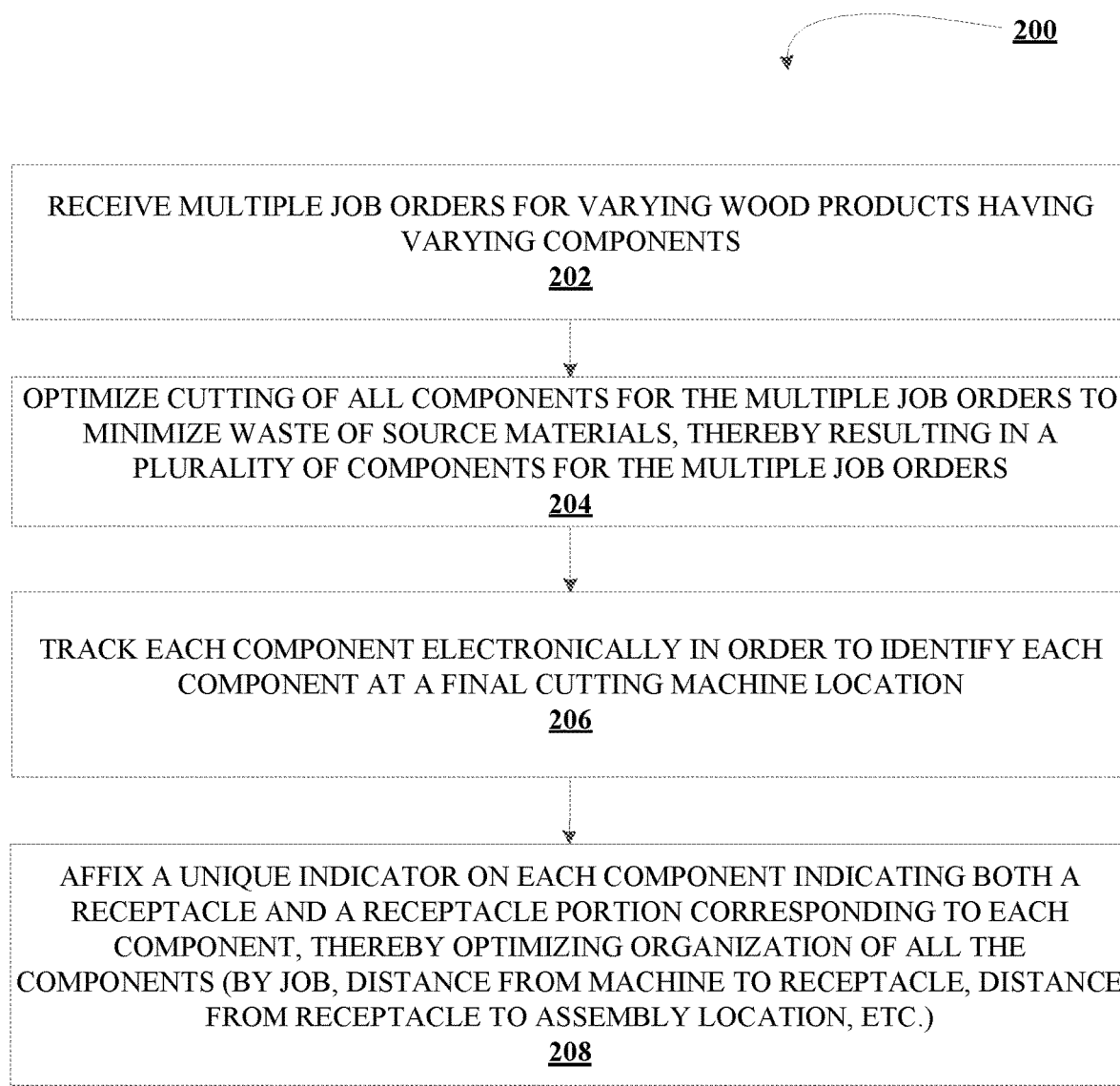
Figure 3:
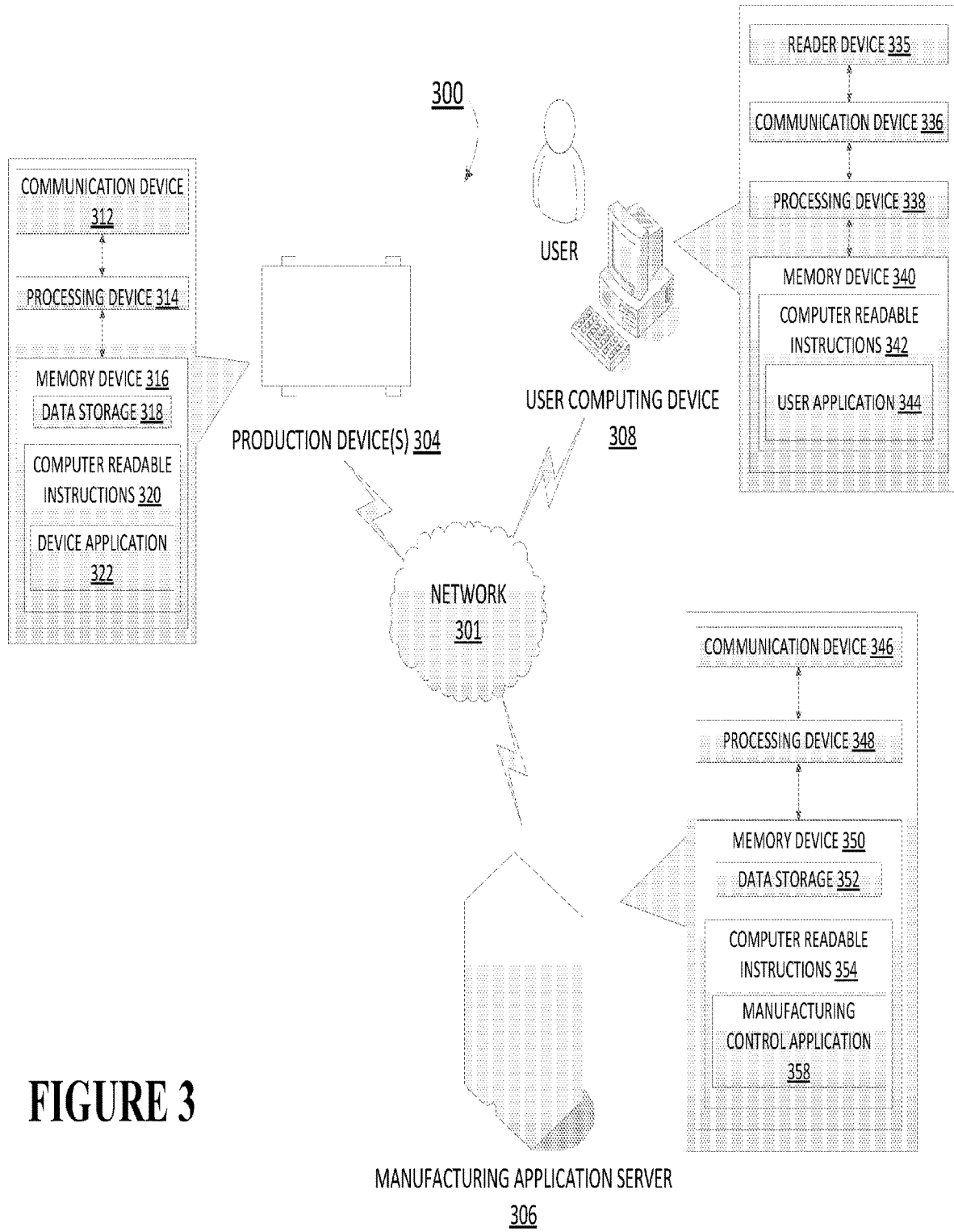

Having thus described embodiments of the invention in general terms, reference will now be made the accompanying drawings, wherein:

FIG. 1 provides a process flow illustrating a high-level summary of an embodiment of the invention;

FIG. 2 is a flowchart illustrating a method 200 for optimizing organization of components for the manufacture of wood products according to embodiments of the invention; and FIG. 3 is a diagram illustrating a system 300 for optimizing organization of components for the manufacturing of wood products is shown according to embodiments of the invention.

DETAILED DESCRIPTION OF EMBODIMENTS OF THE INVENTION

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout. Referring now to the drawings and the listing of machine components set out below, the invention according to a preferred embodiment is described in further detail.

Systems and methods for optimizing organization of components for the manufacture of wood products are disclosed. A component is not necessarily defined by its physical properties (length, width, species or the like), but rather is defined and processed by what it is going to become (part, job, room, etc.). The present invention provides a unique machinery data flow solution leverages data captured across multiple machines in real-time to assign a cart-slot placement for components. Assembly of a final product is done by coordination of components at the end of the manufacturing process.

By example, a number of jobs may be optimized by centrally control of machines to minimize waste during manufacture of a wood product. The cuts of wood are performed in a jumbled fashion such that components for numerous jobs may come out of the final cutting machine in a pile without sufficient organization. In some cases, those components are labelled, such as by a bar-code label affixed to the component at the time of final cutting.

The control system, based on its control of the optimization of cutting numerous jobs concurrently, recognizes that a particular component is associated with a specific job or final product. The control system may cause an organization label to be affixed to the component at or after final cutting. The organizational label may include information corresponding to (i) a cart or other receptacle and (ii) a bin, slot or other receptacle portion (aka portion) such that an operator, or in some cases, an automated sorting system, can transport and manipulate the component such that it is physically placed inside the appropriate receptacle and receptacle portion.

In various embodiments of the invention, a receptacle may be associated with multiple jobs or final products, and in other embodiments, a single receptacle is only associated with a single job or final product. In some embodiments, the portions for a single job are assigned to components such that components for a job are organized next to one another within the receptacle, that is, they may be placed side-by-side for ease of retrieval by an operator tasked with assembly a final product from the components.

In some embodiments, the invention includes an optimization of the locations of the receptacles within a workspace such that jobs and components are disposed in a manner to minimize distance from final cutting machine to receptacle for the most components of a job, to minimize distance from a receptacle to a final product assembly cite or otherwise.

In some embodiments of the invention, the receptacles may be built by leveraging the systems and methods described herein prior to beginning projects for customers.

Referring to FIG. 1, a process flow illustrating a high-level summary of the invention is shown. A bill of materials 102 and a cut list 103 may be created and used to initiate an optimized cutting process for a number of jobs. The jobs are performed by one or more production devices 105A, 105B, 105C, and 105D. The control system 110 may control the production devices, thereby cutting of all the components for all the jobs being cut in an optimized fashion so as to minimize waste as described in U.S. Pat. Nos. 9,558,153 10,197,990, both of which are incorporated by reference herein in their entirety. The system electronically tracks the components of the jobs being cut through the entire process and then causes an indicator to be affixed the components at the final cutting device. The indicator corresponds to one of the receptacles 150, each of which has multiple receptacle portions or bins for receiving the components for the jobs.

Referring now to FIG. 2, a flowchart of a method for optimizing organization of components for the manufacture of wood products is shown. The first step is to receive multiple job orders for varying wood products having varying components as represented by block 202. The next step is to optimize cutting of all the components for the multiple job orders to minimize waste of source materials, as represented by block 204. This step results in the plurality of components for the multiple job orders being cut to completion. The next step, as represented by block 206, is to track each component electronically throughout the cutting job (and as each individual component may move from machine to machine within the system) in order to identify each component at a final cutting machine location. Finally, as represented by block 208, the system affixes a unique indicator on each component. This indicator provides both a receptacle and a receptacle portion corresponding to each component. This final step optimizes the organization of all the components, such as by job, distance from machine to receptacle, distance from receptacle to assembly location, and the like. The various steps may be performed manually, automatically, or a combination.

In various embodiments, a number of receptacles (which may also be referred to as "carts") may be distributed throughout a manufacturing environment. Such carts and their respective bins may be identified by the control system and components flowing from initialization of a cutting process may be tracked and organized upon final cutting utilizing the carts and bins.

In some embodiments, an ID sheet may be utilized. The ID sheet may include an "Item" column that corresponds to a final product. Thus, all the "Item 1" components are listed (each is assigned a "#" or ID). For example, an ID for a particular cart or receptacle may be "CID1480," which would correspond to a single cart within the manufacturing environment. In various implementations, multiple items or products may be associated with a single cart, or in other implementations, a single item may be associated with a single cart.

Computer System

Referring now to FIG. 3, a system 300 for optimizing organization of components for the manufacturing of wood products is shown according to embodiments of the invention. The manufacturing application server 306 is operatively coupled, via a network 301, to multiple production device(s) 304, and to the user computing device 308. For purposes for the invention, a production device and manufacturing device may be used interchangeably. It should be noted that the production device may include one or more production devices, such as mechanical devices, machinery and the like (e.g., a router, a ripsaw, a moulder, etc.). It should be further noted that the terms "user computing device" and "user computing system" may be used interchangeably throughout the specification. In this way, the application server 306 can send information to and receive information from the production device 304 and the user computing device 308 to effectively manage the manufacturing process.

Communication between the application server 306 and the production device 304 may be established in various ways. In one specific embodiment of the system, initiating a connection for communication between the production device 304 and other system components may be executed using three software components or modules. A first software component may be associated with the production device 304 such that the software is stored in the memory device 316 and executed by the processing device 314. A second software component may be associated with the application server such that the software is stored in the memory device 350 and executed by the processing device 348.

In one embodiment, establishing a connection for communication may comprise establishing a socket connection. The production device 304 may establish a socket connection with one or more software components stored on the application server 306 by initiating a request for a connection. Upon retrieval of the request, the second software component may create an instance to the data such that the application server 306 boots an instance of a third software component associated with the production device 304 server. To this extent, the production device 304 and application server 306 may establish a client server connection. For example, when the production device 304 wishes to establish a connection, the first software component may send a first character string to the second software component. The first character string may be any alphanumeric combination which requests a new connection between two communication devices. In response to receiving the first character string the second software component may then boot an instance of an executable server file. In one embodiment, the executable server file may exist in the same folder as the second software component. Once the third software component is booted successfully with a connection to the database, it may send its current port setting to the second software component.

Miscellaneous instructions may be sent to and received from the application server 306. Miscellaneous instructions sent to the application server 306 may include, but is not limited to, package printing instruction, package identification instructions, label design information, and machine identification information. Miscellaneous instructions received from the application server 306 may include instructions to provide a display message. The instructions may also be accompanied with an associated port number. It should be noted that, in addition to communicating with the application server 306, production devices 304 may also communicate directly with one or more additional production devices and the user computing device 308. In one embodiment, the application server 306 can send order and/or job information to and receive information from a plurality of production devices 304. As such, the application server 306 may function as a central communication point for managing the product manufacturing process. For example, the application server 306 may receive a plurality of orders and may communicate instructions, associated with processing the order, to the production devices 304. FIG. 3 illustrates only one example of an embodiment of a system environment 300, and it will be appreciated that in other embodiments, one or more of the systems, devices, or servers may be combined into a single system, device, or server, or be made up of multiple systems, devices, or servers.

The network 301 may be a global area network (GAN), such as the Internet, a wide area network (WAN), a local area network (LAN), or any other type of network or combination of networks. The network 301 may provide for wireline, wireless, or a combination of wireline and wireless communication between devices on the network. One or more orders may be made by a plurality of customers online or offline, over the phone, at a merchant's place of business and/or by other transaction means such that the orders are received at the application server 306 and displayed on the user computing device 308. The order may be made by a customer using a computing device or mobile computing device (i.e. smart phone, PDA, or the like) or other types of systems that communicate with the application server 306 to allow the manufacturer to receive and process an order. In other embodiments, the user may access an order stored on the application server 306 and make changes to the order using the user computing device 308 such that the changes are saved in the application server 306 and the updated order information is simultaneously communicated to the production devices 304.

As illustrated in FIG. 3, the application server 306 generally comprises a communication device 346, a processing device 348, and a memory device 350. As used herein, the term "processing device" generally includes circuitry used for implementing the communication and/or logic functions of the particular system. For example, a processing device may include a digital signal processor device, a microprocessor device, and various analog-to-digital converters, digital-to-analog converters, and other support circuits and/or combinations of the foregoing. Control and signal processing functions of the system are allocated between these processing devices according to their respective capabilities. The processing device may include functionality to operate one or more software programs based on computer-readable instructions thereof, which may be stored in a memory device.

The processing device 348 is operatively coupled to the communication device 346 and the memory device 350. The processing device 348 uses the communication device 346 to communicate with the network 301 and other devices on the network 301, such as, but not limited to the user computing device 308 and the production device(s) 304. As such, the communication device 346 generally comprises a modem, server, or other device for communicating with other devices on the network 301.

As further illustrated in FIG. 3, the application server 306 comprises computer-readable instructions 354 stored in the memory device 350, which in one embodiment includes the computer-readable instructions 354 of an application 358. In some embodiments, the memory device 350 includes data storage 352 for storing data related to customer orders and/or manufacturing information including but not limited to data created and/or used by the application 358 or the user. The data storage 352 may also store real-time update information for production device(s), manufacturer inventory, order history, production statistics and the like.

In the embodiment illustrated in FIG. 3 and described throughout much of this specification, the manufacturing control application 358 allows the user to interact with the system. First, manufacturing control application 358 allows a user to interact with the customer orders and manage the production process, via the production device 304. Next, the application 358 allows the user to receive real-time updates related to the status of a job and/or a plurality or orders. Both sending and receiving job and/or order information may be performed by a using an interface, such as a user interface associated with production device 304 or user computing device 308, provided from the application 358 via a network 301.

In some embodiments, the manufacturing control application 358 allows the user to communicate with the production device 304, to indicate manual changes in the production process. This communication may be in the form of text communications, voice communications, or the like. Typically, the production process is controlled by instructions created via the application server 306, but in some instances the user may interject and manually alter the production process. The manufacturing control application 358 may receive manufacturing information related to a job via the user computing device 308. The user may also use the user computing device 308 to query the real-time status of an order and/or job.

The jobs may be associated with one or more customer orders. This is largely due to the high efficiency that is yielded when grouping one or more orders for production. In this way, the orders are produced as a single job versus individually. In a specific embodiment, the order may be grouped based on like species.

The user, through the user computing device 308, may provide the manufacturing control application 358 data with respect to product manufacturing. The manufacturing control application 358 may then store the data related to the user input such as, but not limited to order cancellations, order amendments, or the like In this way, the manufacturing control application 358 may have access to all real-time information being received by the user. In an instance that the priority rank has been changed the manufacturing control application 358 may queue updated instructions to be sent to the production devices 304. In one embodiment, the manufacturing control application 358 may detect a favorable combination of order components that will further optimize the production in light of the updated instructions.

The manufacturing control application 358 may also receive data from the user computing device 308. The manufacturing control application 358 may determine an optimal production plan for manufacturing the plurality of orders. The data stored within the manufacturing control application 358 provides computer readable instructions 354 to the processing device 348 to allow for the production of a plurality of jobs associated with one or more orders received by multiple customers. The manufacturing control application 358 stores statistics related to successful job executions as well as statistics related to the efficiency of the overall system.

As illustrated in FIG. 3, the user computing device 308 generally comprises a reader device 335, a communication device 336, a processing device 338, and a memory device 340. The reader device 335 is operatively coupled to the processing device 338, communication device 336, and the memory device 340. The user computing device 308 may include a reader device 335 to receive order information from the user. Such a reader device 335 may include a magnetic strip reader, a barcode scanner, a radio frequency (RF) reader, a character recognition device, a magnetic ink reader, a processor for interpreting codes presented over an electrical or optical medium, a biometric reader, a wireless receiving device, and/or the like. In some embodiments, the reader device 335 receives information that may be used to manage the overall production process and communicates the information via the communication device 336 over a network 301, to other systems such as, but not limited to the application server 306 and/or the production device(s) 304. As such, the communication device 336 generally comprises a modem, server, or other device for communicating with other devices on the network 301.

As further illustrated in FIG. 3, the user computing device 308 comprises computer-readable instructions 342 stored in the memory device 340, which in one embodiment includes the computer-readable instructions 342 of a user application 344. A user computing device 308 may refer to any device used to interact with the application server 306, either from the manufacturer's perspective and/or a customer's perspective. In some embodiments, the user computing device 308 may refer only to a user's device, in other embodiments it refers only to a plurality or user devices, and in yet other embodiments, it refers to both a user device interacting with other devices to perform a job. For example, in one embodiment, the user computing device 308 refers to the user computing device configured to communicate with a production device 304, whereas in other embodiments, the user computing device 308 refers to the production device 304 configured to communicate with a user computing device 308, and in yet other embodiments, the user computing device 308 refers to both the user computing device and the production device(s) 304 configured to communicate with each other to carry out a job. In one embodiment, the user computing device 308 may be a kiosk or special terminal for managing orders.

In some embodiments, a user computing device 308 is or includes an interactive computer terminal that is configured to initiate, complete, and/or facilitate one or more real-time order activations. A user computing device 308 could be or include any device that a user may use to interact with the application server 306, such as, but not limited to, a computer, (e.g., a personal computer, tablet computer, desktop computer, server, laptop, or the like), a mobile device (e.g., a smartphone, cellular phone, personal digital assistant (PDA) device, MP3 device, personal GPS device, or the like), and/or various combinations of the foregoing.

In some embodiments, a user computing device 308 is operated in a manufacturing warehouse. In other embodiment, the user computing device 308 may be operated remotely such that the user computing device 308 is not located in the manufacturing facility. In accordance with some embodiments, the user computing device 308 is not owned by the manufacturer. Rather, in some embodiments, the user computing device 308 is owned by a manufacturing company. In yet other embodiments, the user computing device 308 is owned by a third party providing functionality to facilitate and manage a manufacturing process in accordance with embodiments of the invention described herein.

In the embodiment illustrated in FIG. 3, the user application 344 allows the user computing device 308 to be linked to the application server 306 to communicate, via a network 301. Information related to the order being made, such as the customer name, quoted cost of the order, product, quantity, sizes, species and the like may be displayed on the user computing device 308. The user application 344 may provide the manufacturing control application 358 with user input related to the manufacturing process, such that the manufacturing control application 358 may determine an optimal plan for manufacturing a plurality of orders.

The user application 344 may also receive information from the application server 306. The user application 344, in some embodiments, may receive an order from the manufacturing control application 358, such that they user application 344 may display the order to the user on a display on the user computing device 308. In this way, the user may receive an option to alter an order that the system is already in the process of manufacturing. The order may be displayed on the user computing device 308 such that the user may make changes to the order in real-time as the order is being produced.

FIG. 3 also illustrates a production device 304. The production device 304 may include a communication device 312, a processing device 314, and a memory device 316. The processing device 314 is operatively coupled to the communication device 312 and the memory device 316. The processing device 314 uses the communication device 312 to communicate with the network 301 and other devices on the network 301, such as, but not limited to the user computing device 308, the application server 306. As such, the communication device 312 generally comprises a modem, server, or other device for communicating with other devices on the network 301.

As further illustrated in FIG. 3, the production device 304 may include computer-readable instructions 320 stored in the memory device 316, which in one embodiment includes the computer-readable instructions 320 of a device application 322. A production device 304 may be or include any mechanical device and/or machinery including, but not limited to moulder(s), routers, cross cut saws, rip cut saws, coping machines, forklifts, or the like (e.g., a 5-axis router).

As described herein, a system and method for optimizing the organization of components for the manufacture of wood products have been described with reference to specific embodiments and examples. Various details of the invention may be changed without departing from the scope of the invention. Furthermore, the foregoing description of the preferred embodiments of the invention and best mode for practicing the invention are provided for the purpose of illustration only and not for the purpose of limitation, the invention being defined by the claims.

CONCLUSION

As will be appreciated by one skilled in the art, aspects of the present embodiments of the invention may be embodied as a system, method or computer program product. Thus, embodiments of the present invention are described herein with reference to flowchart illustrations and/or block diagrams of methods, systems, and computer program products. Like numbers refer to like elements throughout. It may be understood that each block of the flowchart illustrations and/or block diagrams, and/or combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create mechanisms for implementing the functions/acts specified in the flowchart and/or block diagram block or blocks.

The steps and/or actions of a method or algorithm described in connection with the embodiments disclosed herein may be embodied directly in hardware, in a software module executed by a processor, or in a combination of the two. Accordingly, aspects of the present invention may take the form of an entirely hardware embodiment, an entirely software embodiment (including firmware, resident software, micro-code, or the like) or an embodiment combining software and hardware aspects that may all generally be referred to herein as a "circuit," "module" or "system." Furthermore, aspects of the present embodiments of the invention may take the form of a computer program product embodied in one or more computer readable medium(s) having computer readable program code embodied thereon.

A software module may reside in RAM memory, flash memory, ROM memory, EPROM memory, EEPROM memory, registers, a hard disk, a removable disk, a CD-ROM, or any other form of storage medium known in the art. An exemplary storage medium may be coupled to the processor, such that the processor can read information from, and write information to, the storage medium. In the alternative, the storage medium may be integral to the processor. Further, in some embodiments, the processor and the storage medium may reside in an Application Specific Integrated Circuit (ASIC). In the alternative, the processor and the storage medium may reside as discrete components in a computing device. Additionally, in some embodiments, the events and/or actions of a method or algorithm may reside as one or any combination or set of codes and/or instructions on a machine-readable medium and/or computer-readable medium, which may be incorporated into a computer program product.

If implemented in software, the functions may be stored or transmitted as one or more instructions or code on a computer-readable medium. Computer-readable media includes both computer storage media and communication media including any medium that facilitates transfer of a computer program from one place to another. Any combination of one or more computer readable medium(s) may be utilized. The computer readable medium may be a computer readable signal medium or a computer readable storage medium. A storage medium may be any available media that can be accessed by a computer. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Also, any connection may be termed a computer-readable medium. For example, if software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. "Disk" and "disc", as used herein, include compact disc (CD), laser disc, optical disc, digital versatile disc (DVD), floppy disk and Blu-ray disc where disks usually reproduce data magnetically, while discs usually reproduce data optically with lasers. Combinations of the above should also be included within the scope of computer-readable media.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

These computer program instructions may also be stored in a computer-readable medium that can direct a computer or other programmable data processing apparatus to function in a particular manner, such that the instructions stored in the computer readable memory produce an article of manufacture including instruction means which implement the function/act specified in the flowchart and/or block diagram block(s). Program code embodied on a computer readable medium may be transmitted using any appropriate medium, including but not limited to wireless, wireline, optical fiber cable, RF, or the like, or any suitable combination of the foregoing. Computer program code for carrying out operations for aspects of the present embodiments of the invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the flowchart and/or block diagram block(s). Alternatively, computer program implemented steps or acts may be combined with operator or human implemented steps or acts in order to carry out an embodiment of the invention.

According to various embodiments of the invention, a computing device used by a user has a memory device configured to store computer-executable code and a processing device in communication with the memory device. The processing device is configured to execute computer-executable code stored on the memory device to communicate with one or more production interfaces, the one or more production interfaces associated with one or more mechanical devices and/or machinery used in the production process. In some embodiments, it also provides the user with options to activate, change, and/or prioritize orders that have been received. In some embodiments, it also provides the user information regarding the current status of one or more orders. In some embodiments, it also provides the user an option of seamlessly managing the production of one or more jobs associated with a plurality of orders.

According to some embodiments of the invention, a processing device of the computing device is configured to access a plurality of orders stored in the memory device, and analyze each order to determine what is needed to produce the order and how the orders can be combined into one job that will optimize the resources and materials being used. In some such embodiments, the computing device also determines whether multiple orders can be combined into one batch or job.

As used herein, a "memory device" or "memory" generally refers to a device or combination of devices including one or more forms of non-transitory computer-readable media for storing instructions, computer-executable code, and/or data thereon. Computer-readable media is defined in greater detail herein below. It will be appreciated that, as with the processing device, each communication interface and memory device may be made up of a single device or many separate devices that conceptually may be thought of as a single device.

Although embodiments of the invention described herein are generally described as involving a manufacturing entity, it will be understood that this invention may involve one or more persons, organizations, businesses, merchants and/or other institutions, services providers or the like that implement one or more steps, one or more processes, and/or one or more portions of one or more of the embodiments described and/or contemplated herein, and/or or one or more steps or processes not described herein.

While the foregoing disclosure discusses illustrative embodiments, it should be noted that various changes and modifications could be made herein without departing from the scope of the described aspects and/or embodiments as defined by the appended claims. Additionally, all or a portion of any embodiment may be utilized with all or a portion of any other embodiment, unless stated otherwise. Furthermore, while certain exemplary embodiments have been described and shown in the accompanying drawings, it is to be understood that such embodiments are merely illustrative of and not restrictive on the broad invention, and that this invention is not be limited to the specific constructions and arrangements shown and described, since various other changes, combinations, omissions, modifications and substitutions, in addition to those set forth in the above paragraphs, are possible. Those skilled in the art will appreciate that various adaptations and modifications of the just described embodiments can be configured without departing from the scope and spirit of the invention. Therefore, it is to be understood that, within the scope of the appended claims, the invention may be practiced other than as specifically described herein.

Although many embodiments of the invention have just been described above, the invention may be embodied in many different forms and should not be construed as limited to the embodiments set forth herein; rather, these embodiments are provided so that this disclosure will satisfy applicable legal requirements. Also, it will be understood that, where possible, any of the advantages, features, functions, devices, and/or operational aspects of any of the embodiments of the invention described and/or contemplated herein may be included in any of the other embodiments of the invention described and/or contemplated herein, and/or vice versa. In addition, where possible, any terms expressed in the singular form herein are meant to also include the plural form and/or vice versa, unless explicitly stated otherwise.

What is claimed is:

1. A system for optimizing the organization of components for the manufacture of wood products, the system comprising:
   (a) one or more memory devices; and
   (b) one or more processing devices operatively coupled to the memory device, wherein the one or more processing devices are configured to execute computer-readable computer program code to:
   (i) receive a plurality of job orders for distinct wood products having varying components;
   (ii) optimize cutting of all components for the plurality of job orders to minimize waste of source materials, thereby resulting in a plurality of components for the plurality of job orders;
   (iii) track each component electronically in order to identify each component at a final cutting machine location; and
   (iv) affix a unique indicator on each component indicating both a (i) receptacle and a (ii) receptacle portion corresponding to each component, thereby optimizing organization of all the components by at least one of job, distance from machine to receptacle, and distance from receptacle to assembly location.

2. The system of claim 1, further comprising:
   one or more production devices operatively coupled with the one or more processing devices.

3. The system of claim 2, wherein the one or more processing devices are configured to execute computer-readable computer program code to:
   control one or more actions of the one or more production devices.

4. The system of claim 1, wherein the one or more processing devices are configured to execute computer-readable computer program code to:
   create a plurality of unique indicators for affixation on each component.

5. The system of claim 1, wherein the one or more processing devices are configured to execute computer-readable computer program code to:
track each component electronically by scanning each component to identify each component by visible characteristics or collocated identifier.

6. The system of claim 1, wherein the one or more processing devices are configured to execute computer-readable computer program code to:
track each component electronically by scanning a collocated identifier comprising an RFID or near field communication (NFC) device.

7. The system of claim 1, wherein the one or more processing devices are configured to execute computer-readable computer program code to:
track each component electronically by scanning a readable indicia comprising a barcode or Quick Response (QR) code.

8. A method for optimizing the organization of components for the manufacture of wood products, the method comprising:
(a) receiving a plurality of job orders for distinct wood products having varying components;
(b) optimizing cutting of all components for the plurality of job orders to minimize waste of source materials, thereby resulting in a plurality of components for the plurality of job orders;
(c) tracking each component electronically in order to identify each component at a final cutting machine location; and
(d) affixing a unique indicator on each component indicating both a (i) receptacle and a (ii) receptacle portion corresponding to each component, thereby optimizing organization of all the components by at least one of job, distance from machine to receptacle, and distance from receptacle to assembly location.

9. The method of claim 8, wherein the cutting is performed by one or more production devices.

10. The method of claim 8, further comprising:
controlling one or more actions of the one or more production devices.

11. The method of claim 8, further comprising:
creating a plurality of unique indicators for affixation on each component.

12. The method of claim 8, further comprising:
tracking each component electronically by scanning each component to identify each component by visible characteristics or collocated identifier.

13. The method of claim 8, further comprising:
tracking each component electronically by scanning a collocated identifier comprising an RFID or NFC device.

14. The method of claim 8, further comprising:
tracking each component electronically by scanning a readable indicia comprising a barcode or Quick Response (QR) code.

15. A computer program product for optimizing the organization of components for the manufacture of wood products, the computer program product comprising: a non-transitory computer readable medium comprising computer executable program code stored therein, wherein the computer executable program code comprises:
(a) a first executable portion configured to receive a plurality of job orders for distinct wood products having varying components;
(b) a second executable portion configured to optimize cutting of all components for the plurality of job orders to minimize waste of source materials, thereby resulting in a plurality of components for the plurality of job orders;
(c) a third executable portion configured to track each component electronically in order to identify each component at a final cutting machine location; and
(d) a fourth executable portion configured to affix a unique indicator on each component indicating both a (i) receptacle and a (ii) receptacle portion corresponding to each component, thereby optimizing organization of all the components by at least one of job, distance from machine to receptacle, and distance from receptacle to assembly location.

16. The computer program product of claim 15, wherein the computer executable program code further comprises:
a fifth executable portion configured to control one or more actions of one or more production devices.

17. The computer program product of claim 15, wherein the computer executable program code further comprises:
a fifth executable portion configured to create a plurality of unique indicators for affixation on each component.

18. The computer program product of claim 15, wherein the computer executable program code further comprises:
a fifth executable portion configured to track each component electronically by scanning each component to identify each component by visible characteristics or collocated identifier.

19. The computer program product of claim 15, wherein the computer executable program code further comprises:
a fifth executable portion configured to track each component electronically by scanning a collocated identifier comprising an RFID or NFC device.

20. The computer program product of claim 15, wherein the computer executable program code further comprises:
a fifth executable portion configured to track each component electronically by scanning a readable indicia comprising a barcode or Quick Response (QR) code.

* * * * *